under 35 U.S.C. 154(b) by 0 days.

United States Patent
Xiao et al.

(10) Patent No.: US 6,534,052 B1
(45) Date of Patent: Mar. 18, 2003

(54) CARDIAC FUNCTION COMPRISING IMPLANTATION OF EMBRYONIC STEM CELL IN WHICH DIFFERENTIATION HAS BEEN INITIATED

(76) Inventors: Yong-Fu Xiao, 26 Pequot Rd., Wayland, MA (US) 01778; James P. Morgan, 56 Norwood Ave., Newton Centre, MA (US) 02459

( * ) Notice: Subject to any disclaimer, the term of this patent is extended or adjusted under 35 U.S.C. 154(b) by 0 days.

(21) Appl. No.: 09/655,124

(22) Filed: Sep. 5, 2000

(51) Int. Cl.[7] ..................... A01N 63/00; A61K 48/00; C12N 5/00; C12N 5/02
(52) U.S. Cl. ..................... 424/93.2; 435/325; 435/373; 435/377
(58) Field of Search ................. 435/325, 373, 435/377; 424/93.2

(56) References Cited

U.S. PATENT DOCUMENTS

| | | | |
|---|---|---|---|
| 5,639,618 A | 6/1997 | Gay ..................... 435/7.21 |
| 5,843,780 A | 12/1998 | Thomson ................ 435/366 |
| 6,146,888 A | 11/2000 | Smith et al. ............. 435/325 |
| 6,200,806 B1 | 3/2001 | Thomson ................ 435/366 |
| 6,280,718 B1 | 8/2001 | Kaufman et al. ......... 424/93.1 |

OTHER PUBLICATIONS

Klug. M.G. et al. Genetically Selected Cardiomyocytes from Differentiating Embryonic Stem Cells For Stable Intracardiac Grafts. Journal of Clinical Investigation. vol. 98, No. 1, Jul. 1996, pp. 216–224.*

Odorico et al., Stem Cells 19:193–204 (2001).
Schuldiner et al., PNAS 97:11307–11312 (2000).
Pera et al., Human embryonic stem cells, 2000, Journal of Cell Science, vol. 113, pp. 5–10.*
"Stem Cells: A Primer", National Institutes of health, May 2000.
Chapter 3, "The Human Embryoic Stem Cell and The Human Embryonic Germ Cell", in Stem Cells, National Institutes of Health, 2000.
Appendix C:"Human Embryonic Stem Cells And Human Embryonic Germ Cells", in Stem Cells, National Institute of Health, 2000.
"NIH Human Embryonic Stem Cell Registry", National Institutes of Health, 2001.

* cited by examiner

Primary Examiner—Deborah Crouch
Assistant Examiner—Thaian N. Ton
(74) Attorney, Agent, or Firm—David Prashker

(57) ABSTRACT

The present invention is a method for markedly improving cardiac function and repairing heart tissue in a living mammalian subject after the occurrence of a myocardial infarction. The method is a surgical technique which introduces and implants mammalian embryonic stem cells into the infarcted area of the myocardium. After implantation, the embryonic stem cells form stable grafts and survive indefinitely within the infarcted area of the heart in the living host. The demonstrated beneficial effects of the method include a decreased infarcted area and improved cardiac function as assessed by hemodynamic and echocardiographic measurements.

4 Claims, 5 Drawing Sheets

CARDIAC FUNCTION COMPRISING IMPLANTATION OF EMBRYONIC STEM CELL IN WHICH DIFFERENTIATION HAS BEEN INITIATED

RESEARCH SUPPORT

The research effort and investigations described hereinafter comprising the present invention were supported by a grant from the Cardiovascular Research Endowment Fund.

FIELD OF THE INVENTION

The present invention is concerned generally with myocardial infarctions of the heart and the damage caused to the heart of a living mammalian subject by such infarctions; and is particularly directed to methods and means for improving cardiac function and the potential repair of infarcted areas of the heart after the occurence of a myocardial infarction.

BACKGROUND OF THE INVENTION

Myocardial infarction (MI) is a life-threatening event that may cause cardiac sudden death and heart failure. Despite considerable advances in the diagnosis and treatment of heart disease, cardiac dysfunction after MI is still the major worldwide cardiovascular disorder that is increasing in incidence, prevalence, and overall mortality[1]. After acute myocardial infarction, the damaged cardiomyocytes are gradually replaced by fibrotic non-contractile tissue. The developing ventricular dysfunction is primarily due to a massive loss of cardiomyocytes. It is widely accepted that adult cardiomyocytes have little regenerative capability. Therefore, the loss of cardiac myocytes after MI is irreversible. Finding new effective approaches to improve cardiac dysfunction after MI remains a major therapeutic challenge.

Cell transplantation has emerged as a potentially new approach of repairing damaged myocardium for recent several years. Transplanted cardiomyocytes have been shown to survive, proliferate, and connect with the host myocardium in murine models[2]. Li and his coworkers[3,4] demonstrated that transplanted fetal cardiomyocytes could form new cardiac tissue within the myocardial scar induced by cryoinjury and improve heart function, but the transplanted allogenic cells survived for only a short period in the recipient heart due to immunorejection[5]. Bishop et al.[6] reported that the embryonic myocardium of rats can be implanted and cultured in oculo and demonstrated that the engrafted embryonic cardiomyocytes proliferated and differentiated in a recent review, Heschler et al.[7] pointed out that pluripotent embryonic stem (ES) cells cultivated within embryonic bodies reproduce highly specialized phenotypes of the cardiac tissue. Most of the biological and pharmacological process of cardiac-specific ion currents are expressed in cardiomyocytes developed in vitro from pluripotent ES cells, which were similar to those previously described in adult cardiomyocytes or neonatal mammalian heart cells[7,8] However the significance of ES cell transplantation in postinfarcted failing hearts remains to be examined.

Several studies have demonstrated the feasibility of engrafting exogenously supplied cells into host myocardium, including fetal cardiomyocytes[2] derived from artial tumor (ATT)[15], satellite cells[16], or bone marrow cells[17]. These engrafted cells have been histologically identified in normal myocardium up to 4 months after transplantation[15] Gap junctions have been found between the engrafted fetal cardiomyocytes and the host myocardium[2], thereby raising the possibility of electrical-contraction coupling between transplanted cells and the host tissue. Recently, myocyte transplantation has been extended into ischemically damaged myocardium with coronary artery occlusion in rats[0,8], or with cryoinjury in rats[3,4] and dogs[16].

Nevertheless, despite all these research efforts and reported investigations, very little progress has been made to date in methods and cellular materials which might directly or markedly improve cardiac function in the living host after the occurrence of a myocardial infarction; or might serve as a cell transplantation therapeutic technique for effecting at least a partial repair of the infarcted area of the myocardium; or might offer a potential long-term improvement of the damaged heat tissue in the afflicted host subject. Were such an effective methodology to be generated and empirically demonstrated, such a development would be regarded as a major advance and unforeseen event by physicians and surgeons working in the field of cardiology.

SUMMARY OF THE INVENTION

The present invention provides a method for improving cardiac function in a living mammalian subject after the occurrence of a myocardial infarct within the heart tissue, said method comprising the steps of:

obtaining a plurality of undifferentiated mammalian embryonic stem cells then maintained in a culture media suitable for subsequent initiation of cell differentiation;

introducing said cultured mammalian embryonic stem cells to at least a portion of the previously infarcted area of the heart tissue in the living subject; and allowing said introduced mammalian embryonic stem cells to differentiate in-situ as viable cells situated within the previously infarcted area of the heart tissue, whereby the cardiac function of the heart in the living subject becomes markedly improved.

BRIEF DESCRIPTION OF THE FIGURES

The present invention may be more easily understood and better appreciated when taken in conjunction with the accompanying drawing, in which.

DETAILED DESCRIPTION OF THE INVENTION

Figure 1:
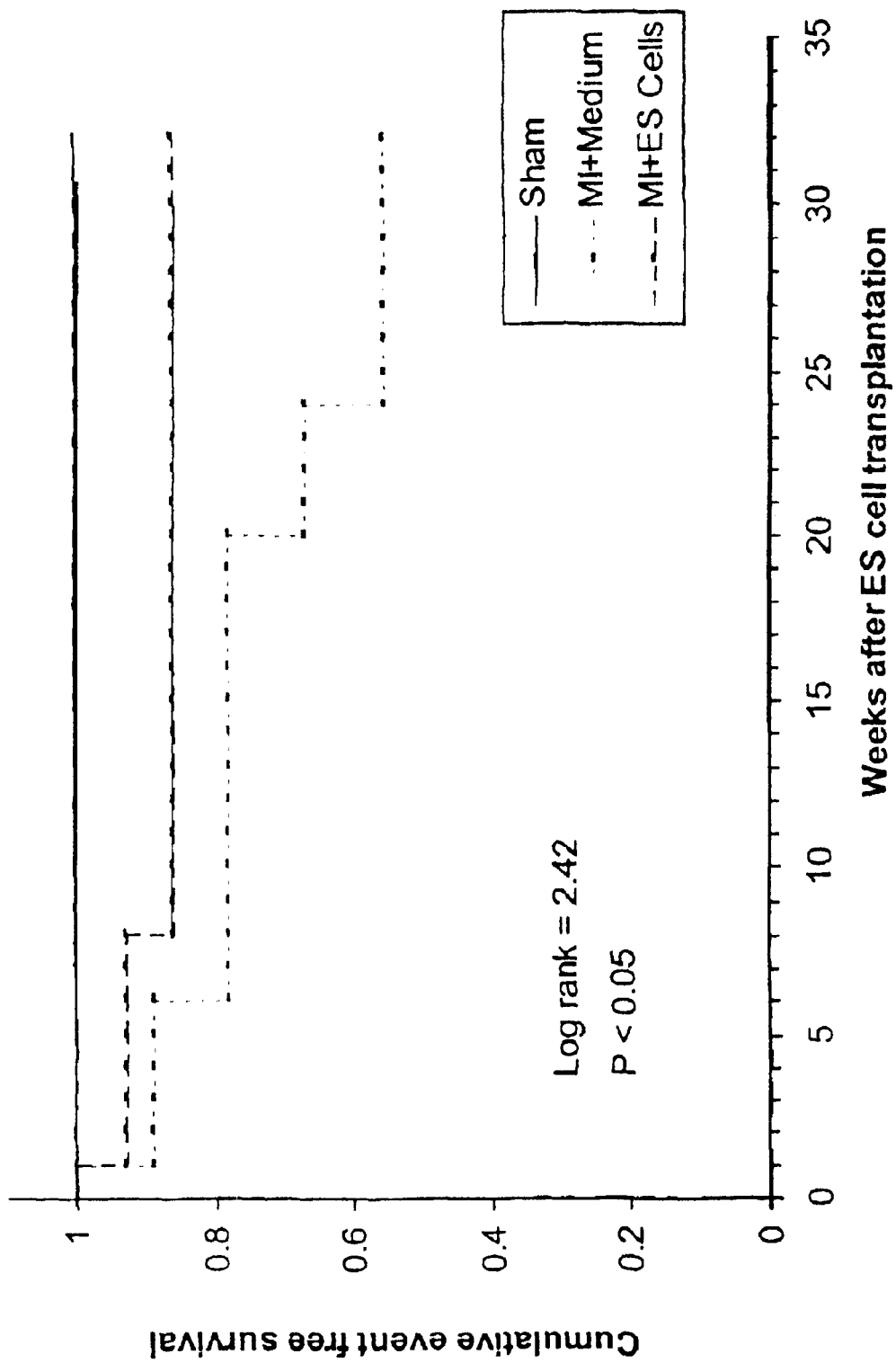
FIG. 1 is a graph showing the cumulative event free survival rate for rats up to 32 weeks after the occurrence of a mycocardial infarction as a function of receiving or not receiving an implantation of embryonic stem cells postinfarction.

The present invention is a method for markedly improving cardiac function and repairing heart tissue in a living mammalian subject after the occurrence of a myocardial infarction. The method is a surgical technique which introduces and implants mammalian embryonic stem cells into the infarcted area of the myocardium. After implantation, the embryonic stem cells form stable grafts and survive indefinitely within the infarcted area of the heart in the living host. The demonstrated beneficial effects of the method include a decreased infarcted area and improved cardiac function as assessed by hemodynamic and echocardiographic measurements.

To demonstrate the range and variety of mammalian embryonic stem cells; the manner of obtaining, maintaining, and preparing embryonic stem cells in vitro; the surgical techniques employed for implantation of cells into the infarcted area of the heart; and the major beneficial effects and therapeutic clinical improvements resulting from the use of this methodology, some illustrative in vivo and in vitro experiments were performed. These experiments and the resulting analytical and clinical data will serve merely to demonstrate the utility, the efficacy, and the range of embodiments for the present invention.

While the individual design and obtained empirical results for these in vivo and in vitro experiments are limited in scope and content, it will be expressly understood that these empirical data and the experimental details described hereinafter do not either restrict or limit the source, type, nature or phenotypic characterisitcs of the mammalian embryonic stem cells which may be usefullly employed when practicing the method; nor is the type, genus or species of mammalian subject or recipient circumscribed or confined so long as the living host has been afflicted with a myocardial infarction previously. To the contrary, these experiments and empirical results are merely representative of the variety of mammalian host subjects which can be therapeutically treated and the diversity of mammalian embryonic cells which can be advantageously prepared and implanted for therapeutic purposes.

EXPERIMENTS AND EMPIRICAL DATA

The experiments and data described hereinafter employ a range of clinical and diagnostic evaluation techniques and systems which are conventionally known and used in the medical arts. The reader is presumed to be acquainted and familiar with the field of cardiology in general, the medical condition of myocardial infarction in its gross and cellular apects, and the techniques routinely employed by physicians and surgeons for assessing heart function and diagnosing heart ailments.

MATERIALS AND METHODS

ES Cell Culture

The mouse ES cell line, ES-D3, was obtained from the American Type Culture Collection (ATCC, Manassas, Va.) and maintained with the methods as previously described (Smith A G. 1991). Briefly, ES-D3 cells were cultured in Dulbecco's modified eagle's medium (DMEM) on mitotically inactive mouse embryonic fibroblast feeder cells (ATCC, Manassas, Va.). The medium was supplemented with 15% fetal bovine serum, 0.1 mM β-mercaptoethanol (Sigma, St. Louis, Mo.), and $10^3$ units/ml of leukemia inhibitory factor (LIF) conditioned medium (BRL, Gaithersburg, Md.) to suppress differentiation. To initiate differentiation, ES cells were dispersed with trypsin and resuspended in the medium without supplemental LIF and cultured with the hanging drops (approximate 400 cells per 20 µl) method for 5 days. Then they were seeded into 100-mm cell culture dishes. Beating cardiomyocyte clusters were dissected by use of a sterile micropipette (Klung et al., 1995) and re-cultured for another 2 to 3 days at 37° C. in a humidified atmosphere with 5% $CO_2$. Finally, cultured cells were trypsinized and collected by centrifugation at 500 g for 5-min at room temperature. Collected cells were resuspended in the culture medium with a concentration of $10^6$ cells/ml and were then ready for cell transplantation.

Experimental Myocardial Infarction

Experiments were performed in male Wistar rats (Charles River, Wilmington, Mass.) with an initial body weight of 250–300 g. Myocardial infarction (MI) was created by ligation of the left anterior descending coronary artery as previously described (Min et, al., 1999). Animals were intubated and ventilated with room air by using a small animal ventilator (Harvard Apparatus, South Natick, Mass.) under pentobarbital (60 mg/kg; i.p.) anesthesia. The heart was expressed through a left thoracotomy, and a 6-0 silk ligature was snugly secured around the left anterior descending coronary artery. MI was verified by observing a blanching ischemic area and by a surface ECG recording.

ES Cell Transplantation

ES cell transplantation was performed after induction of MI during the same operation. In ES cell transplanted rats, ES cell suspension (30 µl) were separately injected into 3 different sites of MI hearts with a tuberculin syringe. Two injection sites located at the borders between normal myocardium and the infarcted area. The other injection site was in the infarcted area. Each injection contained 10 µl of the medium with beating ES cells ($10^6$ cells/ml). Control animals received the same MI operation but were only injected with an equivalent volume of cell-free medium. The sham group underwent identical surgery with neither ligation of the coronary artery nor intramyocardial injection. After recovery of spontaneous respiration from anesthesia, each rat was extubated. Antibiotic (benzathine pencillium G 37500 U per rat) was administrated intramuscularly every 2 days for 1 week following surgery, and analgesia (buprenorphine hydrochloride, 0.01 to 0.05 mg/kg body weight) was given subcutaneously every 8 hours for the first 2 days after the operation.

The survival rate was evaluated in all groups during the whole process of the study. The first cohort of rats was studied to evaluate the short-term effects of ES cell transplantation after 6 weeks. The second cohort of animals was studied to investigate the long-term effects of ES cell transplantation after 32 weeks. Each cohort was comprised of the following groups: MI rats transplanted with ES cells (MI+ ES Cells, n=7); MI control rats injected with an equivalent volume of culture medium (MI+Medium, n=5); and sham-operated rats with neither ligation of the coronary artery nor intramyocardial injection (Sham, n=6).

Echocardiographic Studies

On weeks 6 and 32, after transplantation, the animals were anesthetized with pentobarbital. The echocardiographic procedure was performed as previously described (Litwin et al., 1995). A commercially available echocardiographic system equipped with a 12-MHz probe was used for all studies (Hewlett-Packard, Series 5500, Palo Alto, Calif.). Initially, a two-dimensional short-axis view of the left ventricle was obtained at the level of the papillary muscles. After optimizing gain settings and ensuring that the image was on-axis, M-mode tracings were recorded through the anterior and posterior left ventricular (LV) walls at a paper speed of 100 mm/s. This orientation was chosen to allow delineation of wall thickness and motion in infarcted and noninfarcted territories. LV mass was calculated using a standard cube formula which assumed a spherical LV geometry. Relative anterior wall thickness, relative posterior wall thickness, and LV internal dimensions were measured from at least three consecutive cardiac cycles on a M-mode strip chart recording. We also used endocardial fractional shortening and midwall fractional shortening as indices to estimate LV systolic function. The data of M-mode tracings was analyzed using a commercially available off-line analysis system (Cardiac Workstation, Freeland Systems, Louisville, Colo.).

Measurement of Infarct Area

After echocardiographic measurement, the rats were sacrificed to measure infarct size as described in a previous study (Donnelly et al., 1992, Hutter et al., 1996). The chest was opened by a left-sided thoracotomy with pentobarbital deep anesthesia. Evans blue (1%, ~2.5 ml) was injected into the aorta and coronary artery with distribution throughout the ventricular wall proximal to the coronary artery ligation. The heart was then excised immediately and rinsed in water to remove excess dye, the atria and right ventricular free wall were removed, and the remaining left ventricle was sectioned transversely from apex to base into five slices. These samples were incubated in 1.5% triphenyltetrazolium chloride (TTC) solution for 12 minutes, and were fixed in a 10% formalin solution for 24 hours. The epi- and endocardial circumferences of the infarcted area and entire flattened LV were outlined on a transplant sheet. Infarct size (%) was calculated from the ratio of the surface area of the infarcted wall and the entire surface area of the LV.

Hemodynamic and Isometric Contraction Measurement

In another series of experiments (five in each group), rats were anesthetized with ether, and were placed on a thermally controlled-operation plank in a supine position. A 3-0 silk was placed behind the front lower incisors and pulled taut to slightly extend the neck. The right carotid artery was isolated and cannulated with a 3-Fr high-fidelity mikro-tip catheter connected to a pressure transducer (Millar Instruments, Houston, Tex.). The millar mikro-tip catheter was briefly advanced into the left ventricle and then withdrawn to the aortic arch while ventricular pressure was recorded. Left ventricular systolic and end-septum were weighed and normalized by body weight. The ratio was calculated as indices of hypertrophy.

Histological Studies

Subsets of animals (three for each group) were sacrificed at different time points; i.e., 6 and 32 weeks after ES cell transplantation, to evaluate the morphological characteristics. The hearts was quickly removed and washed in ice-cold PBS. The free wall of the left ventricle including the infarcted and periinfarcted regions was embedded in tissue freezing medium (Fisher Scientific, Fair Lawn, N.J.). Frozen tissues were sectioned to 10-$\mu$m slides, and then stained with hematoxylin and eosin. Sections were examined with a Nikon microscope (Nikon microphot-SA, EPI-FL3, 13522, Tokyo, Japan). Images were captured on the Coolsnap system (RS Photometrics, Roper Scientific, Inc. Tucson, Ariz.) at various levels of magnification and saved on a personal computer.

To identify regenerated myocytes from engrafted ES cells, we used an immunofluorescent method to identify $\alpha$-actin muscle isoform, which is present only in fetal cardiomyocytes, but not in normal adult myocytes (Scorsin et al., 1996; Leor et al., 1996). Frozen tissue sections were fixed in aceton (4° C.) for 10 min and incubated with a monoclonal anti-$\alpha$-actin antibody (Sigma, St. Louis, Mo.) for 45 min at room temperature. Sections were washed three times in PBS and incubated with Cy3-conjugated goat anti-mouse IgG (1:400 dilution) (Sigma, St. Louis, Mo.) for 45 min at room temperature. After extensive washing in PBS, slides were mounted with DAPI/Antifade (Oncor, Gaithersburg, Md.). The slices were examined with the use of a Nikon fluorescent microscope.

Statistical Analysis

Results were presented as mean±SEM. Data was evaluated by one-way analysis of variance with repeated measurements. Differences between individual groups were compared by using unpaired Student's t-test. Statistical comparisons between short-term and long-term follow-ups after ES cell transplantation were made by unpaired Student's t-test. Survival during the 32-week trial was analyzed by standard Kaplan-Meier analysis and a statistical comparison between survival curves was made using the log rank test. The criterion used for statistical significance was accepted at the level of P<0.05.

RESULTS

Survival Rate

Survival after the occurrence of a myocardial infarction is the first and most essential criterion. For this purpose, three groups of rats {sham-operated, MI+medium, and MI+ES cells} were followed for thirty two (32) weeks post infarction. The results are graphically shown by FIG. 1.

Survival was significantly reduced in post-MI rats with the cell-free medium injection compared to sham-operated and MI rats with ES cell transplantation. During the 32 week treatment period, 4 of 15 animals died in the MI+Medium group (29%) compared the Sham and MI+ES Cell group (P<0.05). The Kaplan-Meier analysis (FIG. 1) demonstrated a significant improvement in survival in the MI rats with ES cell transplantation, in which 1 of 14 (7.1%) animals died.

Improvement of Left Ventricular Function After ES Cell Transplantation

The effects of ES cell transplantation 6 and 32 weeks after MI on indices of LV remodeling, as well as infarct size, are shown in Table 1. The LV weight, the ratio of LV weight to body weight, was significantly increased in MI-Medium group compared to sham-operated rats. ES cell transplantation significantly decreased infarct size and the degree of LV hypertrophy in infarcted rats in both the 6 week and 32 week follow-ups after MI.

Hemodynamic measurement shows that post-MI rats with the cell-free medium injection resulted in a decrease in LV systolic pressure (LVSP) and maximum rate of rise of pressure (dP/dtmax) (Table 2), but an increase in LV end-diastolic pressure (LVEDP). Compared to the MI+Medium group, the 32 week follow up after ES cell transplantation showed beneficial effects similar to 6 weeks after transplantation in infarcted rats in improvement of cardiac function; i.e., increase of LVSP, dP/dtmax and decrease of LVEDP (FIG. 2).

Figure 2:
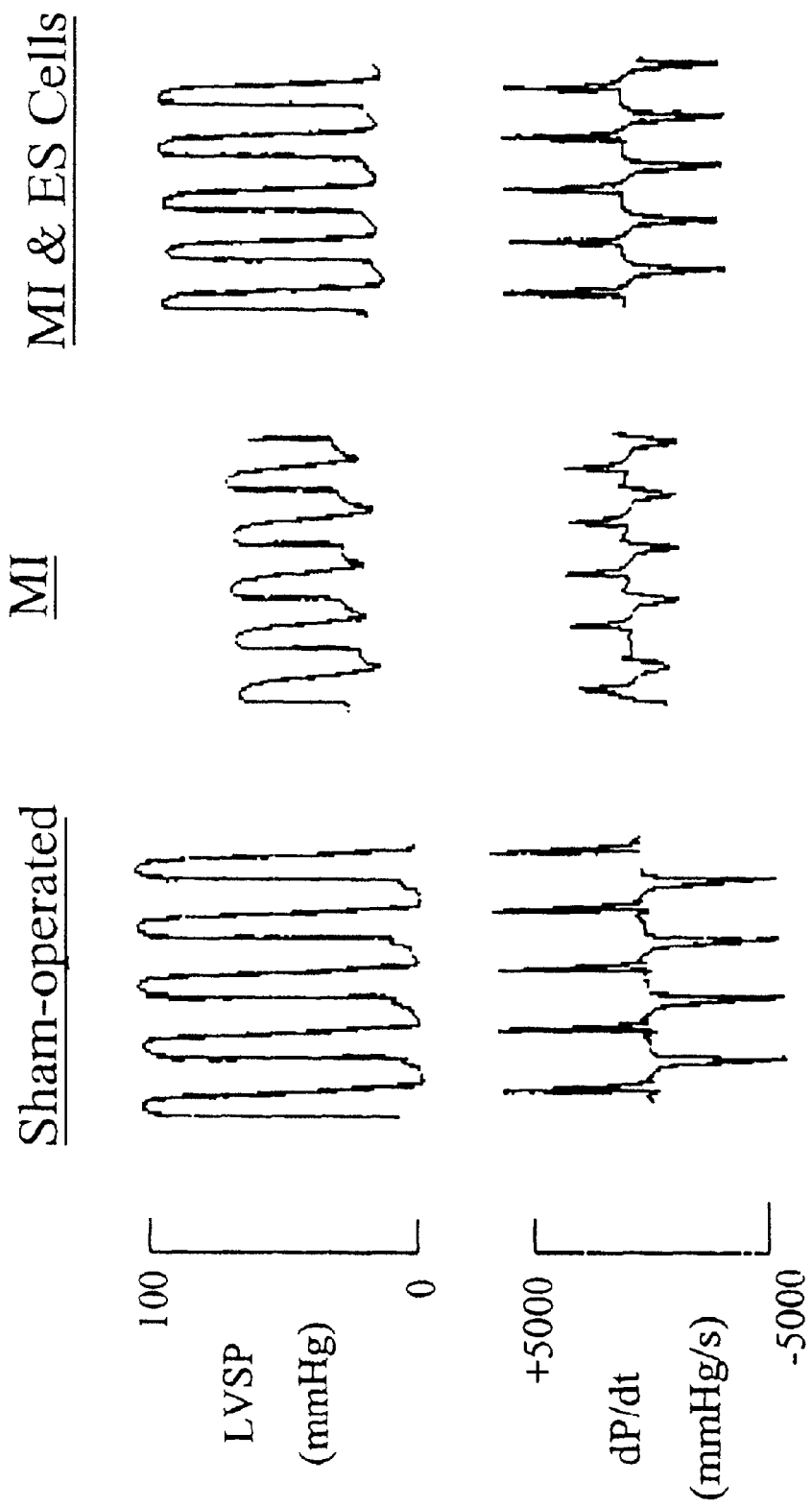
FIGS. 2A–2C are illustrations of continuous chart strip recordings of hemodynamic measurements in anesthetized rats showing the improvement of left ventricular function after embryonic stem cell implantation in the infarcted area of the heart.

FIGS. 2A–2C shows the improvement of left ventricular function after ES cell transplantation post-infarction. FIG. 2 presents continuous chart strip recordings of hemodynamic measursments in anesthetized animals. FIG. 2A illustrates the measurments of sham-operated rats; FIG. 2B represents the measurements of postinfarcted rats injected with the cell-free medium; and FIG. 2C presents the measurements of postinfarcted rats implanted with embryonic stem cells. All measurments were conducted 6 weeks after the MI operation.

TABLE 1

General characteristics of sham-operated and MI rats

| | 6-week follow up | | | 32-week follow up | | |
|---|---|---|---|---|---|---|
| | Sham-I (n = 6) | MI + Medium-I (n = 6) | MI + ES Cells-I (n = 7) | Sham-II (n = 6) | MI + Medium-II (n = 5) | MI + ES Cells-II (n = 7) |
| BW (g) | 433.6 ± 21.4 | 424.7 ± 20.8 | 402.8 ± 18.4 | 623.6 ± 37.3 | 619.5 ± 36.9 | 598.5 ± 46.3 |
| LVW (mg) | 748.4 ± 21.5 | 1005.2 ± 42.3* | 794.6 ± 22.5# | 978.3 ± 26.4 | 1224.3 ± 33.6* | 1143.6 ± 25.4# |
| LVW/BW (mg/g) | 1.6 ± 0.2 | 2.4 ± 0.3* | 1.8 ± 0.2# | 1.5 ± 0.4 | 2.1 ± 0.3* | 1.7 ± 0.3 |
| Infarct size (%) | | 41 ± 3 | 35 ± 2# | | 37 ± 4 | 30 ± 3# |

Values are means ± SE.
Sham-I, sham-operated rats 6 weeks after operation;
Sham-II, sham-operated rats 32 weeks after operation
MI + Medium-I, postinfarcted rats injected with cell-free medium 6 weeks after operation;
MI + Medium-II, postinfarcted rats injected with cell-free medium 32 weeks after operation;
MI + ES Cells-I, postinfarcted rats with ES cell transplantation 6 weeks after operation;
MI + ES Cells-II, postinfarcted rats with ES cell transplantation 32 weeks after operation
BW: body weight;
LVW: left ventricular weight;
LVW/BW: ratio of left ventricular weight against body weight.
*$P < 0.05$;
**$P < 0.01$ MI + Medium-I, MI + ES Cells-I vs. Sham-I or MI + Medium-II, MI + ES Cells-II vs. Sham-II;
$P < 0.05$ MI + ES Cells-I vs. MI + Medium-I or MI + ES Cells-II vs. MI + Medium-II.

TABLE 2

Improvement of left ventricular function after transplantation of ES cells

| | 6-week follow up | | | 32-week follow up | | |
|---|---|---|---|---|---|---|
| | Sham-I (n = 6) | MI + Medium-I (n = 6) | MI + ES Cells-I (n = 7) | Sham-II (n = 6) | MI + Medium-II (n = 5) | MI + ES Cells-II (n = 7) |
| LVSP (mmHg) | 138.4 ± 6.3 | 84.6 ± 5.2** | 103.5 ± 7.4*# | 129.8 ± 5.4 | 80.3 ± 4.3** | 98.6 ± 6.5*# |
| LVEDP (mmHg) | 10.2 ± 0.9 | 21.7 ± 1.8** | 14.4 ± 1.5*# | 8.6 ± 1.0 | 19.2 ± 1.5** | 13.7 ± 1.3*# |
| dP/dt (mmHg/s × 10³) | 8.5 ± 0.7 | 5.6 ± 0.5** | 7.3 ± 0.6# | 9.0 ± 0.9 | 5.8 ± 0.5** | 7.1 ± 0.3# |

Values are means ± SE.
Sham-I, sham-operated rats 6 weeks after operation;
Sham-II, sham-operated rats 32 weeks after operation;
MI + Medium-I, postinfarcted rats injected with cell-free medium 6-week after operation;
MI + Medium-II, postinfarcted rats injected with cell-free medium 32-week after operation;
MI + ES Cells-I, postinfarcted rats transplanted with ES cells 6-week after operation;
MI + ES Cells-II, postinfarcted rats transplanted with ES cells 32-week after operation.
LVSP: the left ventricular systolic pressure;
LVEDP: the left ventricular end-diastolic pressure;
+dP/dt, the raising rate of peak left ventricular systolic pressure.
*$P < 0.05$;
**$P < 0.01$ MI + Medium-I, MI + ES Cells-I vs. Sham-I or MI + Medium-II, MI + ES Cells-II vs. Sham-II;
$P < 0.05$ MI + ES Cells-I vs. MI + Medium-I or MI + ES Cells-II vs. MI + Medium-II.

In vivo 2-dimensional targeted M-mode echocardiographic assessments were obtained in sham-operated and MI rats (Table 3). Echocardiographic studies showed significant differences in LV geometry between rats with MI and sham-operated rats. The inhibition of LV relative anterior and posterior wall thicknesses were comparable in sham-operated rats and MI rats with injection of the medium at 6 weeks after the operation. LV dimension enlarged in the infarcted hearts treated with the cell-free medium in either systole or diastole. The prominent increase in cavity dimensions in the infarcted hearts from the MI control group resulted in a significant decrease in relative anterior and posterior wall thicknesses. Both endocardial fractional shortening and midwall fractional shortening were depressed in MI control rats compared to age-matched sham animals. ES cell transplantation significantly blunted the development of the left ventricular remodeling with a lower ratio of LV weight over body weight than that in MI rats injected with the cell-free medium. These results are similar to the data in table 1 measured in vitro. LV relative anterior and posterior wall thicknesses were increased in MI rats with ES cell transplantation. Likewise, compared to MI rats injected with the cell-free medium, LV diastolic and systolic dimensions decreased in MI rats with ES cell transplantation. The parallel changes in relative wall thickness and cavity diameter resulted in improvement of cardiac systolic function.

TABLE 3

Echocardiographic measurements of left ventricular function in vivo

| | 6-week follow up | | | 32-week follow up | | |
|---|---|---|---|---|---|---|
| | Sham-I | MI + Medium-I | MI + ES Cells-I | Sham-II | MI + Medium-II | MI + ES Cells-II |
| PW th (%) | 72.4 ± 21 | 41.6 ± 14* | 61.3 ± 8# | 79.2 ± 17 | 46.2 ± 7 | 59.5 ± 8*# |
| AW th (%) | 65.2 ± 18 | 40.7 ± 10* | 57.8 ± 9# | 64.4 ± 15 | 39.5 ± 9 | 54.6 ± 10# |
| LVDd (mm) | 7.3 ± 0.4 | 10.0 ± 0.9** | 8.2 ± 0.3# | 8.0 ± 0.3 | 10.5 ± 0.5 | 8.6 ± 0.4# |
| LVDs (mm) | 4.6 ± 0.4 | 7.5 ± 1.1** | 5.8 ± 0.7 | 5.1 ± 0.3 | 7.7 ± 0.8 | 6.2 ± 0.5*# |
| En FS (%) | 36.8 ± 5.4 | 21.0 ± 2.6** | 30.7 ± 4.3# | 36.7 ± 2.5 | 24.2 ± 2.3 | 31.0 ± 1.6# |
| MW FS (%) | 20.6 ± 3.6 | 13.3 ± 1.8* | 17.8 ± 2.6# | 21.1 ± 2.6 | 14.5 ± 2.2 | 17.6 ± 1.2 |
| LV Mass (g) | 0.65 ± 0.1 | 1.10 ± 0.2** | 0.81 ± 0.2# | 0.92 ± 0.1 | 1.38 ± 0.3 | 1.09 ± 0.2# |
| LV Mass/BW (mg/g) | 1.4 ± 0.2 | 2.4 ± 0.2** | 1.7 ± 0.4# | 1.5 ± 0.2 | 2.3 ± 0.2 | 1.8 ± 0.5# |

Values are means ± SE.
Each group represents 5 rats.
PW th, relative posterior wall thickness;
AW th, relative anterior wall thickness;
LVDd, left ventricular diastolic dimension;
LVDs, left ventricular systolic dimension;
En FS, endocardial fractional shortening;
MW FS, midwall fractional shortening;
LV Mass/BW, ratio of left ventricular mass against body weight.
*$P < 0.05$;
**$P < 0.01$ MI + Medium-I and MI + ES Cells-I vs. Sham-I or MI + Medium-II and MI + ES Cells-II vs. Sham-II;
$P < 0.05$ MI + ES Cells-I vs. MI + Medium-I or MI + ES Cells-II vs. MI + Medium-II.

Improvement of Isometric Contractility in Papillary Muscle after ES Cell Transplantation At baseline, the papillary muscles isolated from MI rats injected with the cell-free medium showed a significant decrease in developed tension (FIG. 3). In animals with intramyocardial injection of ES cells, developed tension appeared to be significantly preserved Elevation of extracellular $Ca^{2+}$ levels increased developed tension of papillary muscles isolated from all three groups of rats. The increase in developed tension was concentration-dependent. However, the concentration-response curve of developed tension in MI rats injected with the cell-free medium was significantly shifted downwardly Beta-adrenergic stimulation with cumulative concentrations of isoproterenol induced a pronounced increase in developed tension in papillary muscles isolated from sham-operated rats (FIGS. 3 and 4). In contrast, papillary muscle isolated from MI rats injected with the cell-free medium had no positive inotropic response to isoproterenol stimulation. It is surprising that ES cell transplantation significantly restored the inotropic response to isoproterenol stimulation.

Figure 3B:
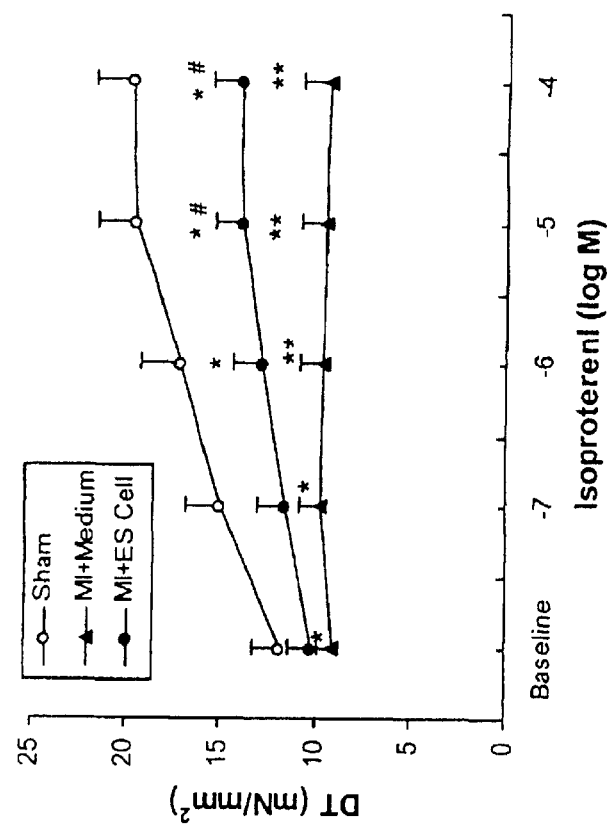
FIGS. 3A and 3B are graphs showing the inotropic response to $Ca^{2+}$ and isoproterenol stimulation after implantation of embryonic stem cells in the infarcted area of the heart.
Figure 3A:
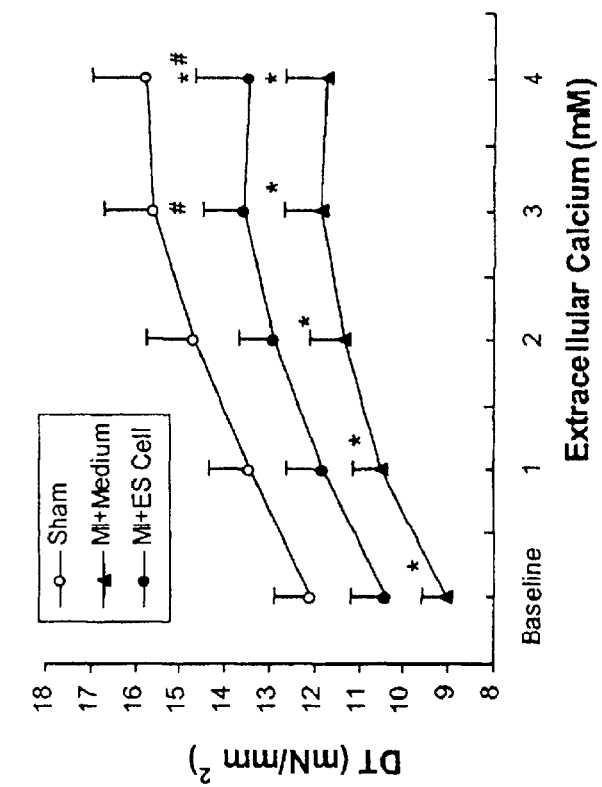
Figure 4:
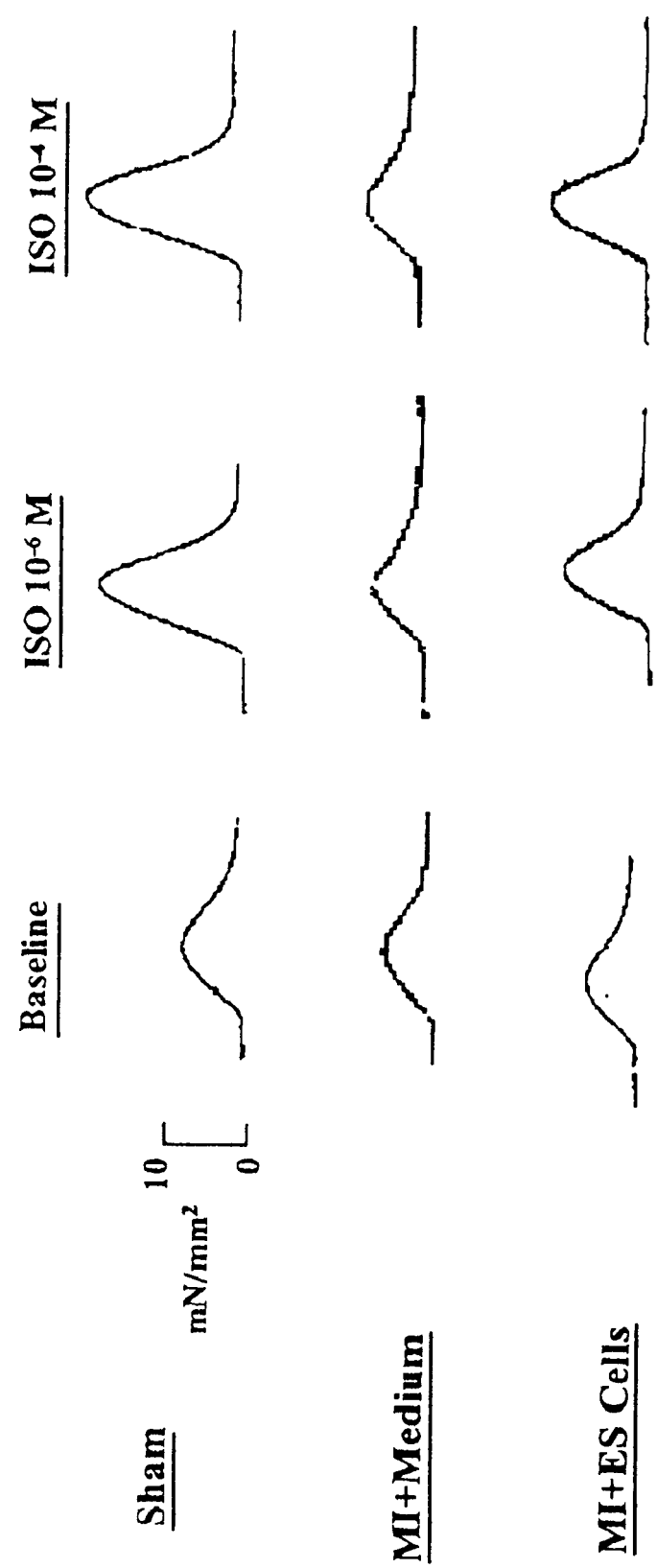
FIGS. 4A–4C are representative drawings showing the improvement of inotropic responsiveness during isoproterenol stimulation on papillary muscle after embryonic stem cell implantation in the infarcted area of the heart.

FIGS. 3A and 3B show the inotrophic response to $Ca^{2+}$ and isoproterenol stimulation after ES implantation. FIG. 3A is a graph illustrating the effects of different extracellular $Ca^{2+}$ levels on developed tension of isolated papillary muscles for the three groups of rats tested 6 weeks post-infarction; and FIG. 3B is a graph showing the effect of different isoproterenol concentrations on developed tension of isolated papillary muscles for sham-operated rats, MI+medium rats, and MI+ES cells rats 6 weeks post-infarction. Sham (n=6); MI+medium (n=6); MI+ES cells (n=7). DT=developed tension produced by the stimulated muscle.

*=P less than 0.05; **=P less than 0.01 vs Sham;
=P less 0.05 vs MI+medium.

FIGS. 4A–4C are original representative recordings showing inotropic responsiveness during isoproterenol stimulation in papillary muscles isolated from rats in the three groups tested. FIG. 4A illustrates the inotropic effects from a sham-operated rat; FIG. 4B illustrates the effect from a postinfarcted rat injected with cell-free medium; and FIG. 4C illustrates the effect from a postinfarcted rat implanted with ES cells. The improvment of inotropic effects of isoproterenol on pappilary muscle after ES cell transplantation is self-evident.

Histological and Immunofluorescent Studies

On survey of hematoxylin-eosin-stained sections with light microscopy, FIG. 5 snows the typical normal myocardium (FIG. 5A) and fibrosis (FIG. 5B) in MI rats injected with the cell-free medium 6 weeks after the MI operation. In ES cell-transplanted MI rats characteristic phenotype of engrafted ES cells was detected in infarcted areas (FIG. 5C). Immunofluorescent techniques confirmed that these grafted cells were clearly distinct from adult cardiomyocytes and infarcted tissue. The viability of the implanted ES cells was identified with strong positive stains of α-actin (FIG. 5D). The α-actin stain was negative for myocardium in sham-operated rats and MI rats injected with cell-free medium.

Figure 5A:
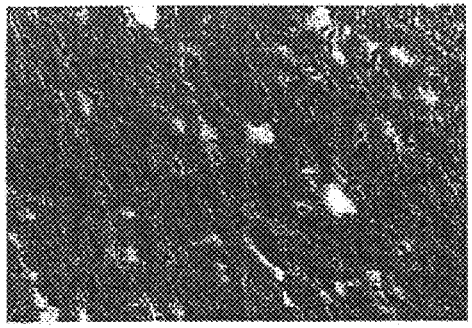
FIGS. 5A–5D are photographs showing the colonization of the infarcted area by grafted cells after implantation of embryonic stem cells in the infarcted area of the heart.
Figure 5B:
Figure 5C:
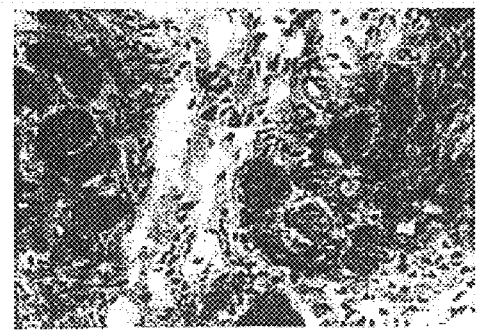
Figure 5D:
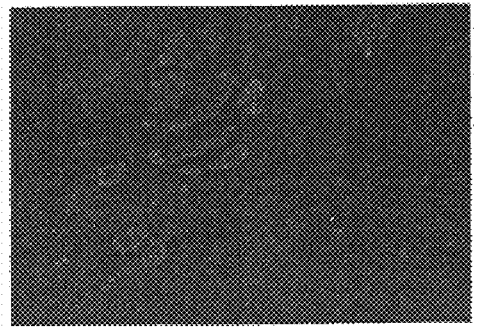

Surrounding scar tissue induced by MI was not stained positively with the α-actin monoclonal antibody. Original magnification ×400. Stains were conducted in rats 6 weeks after the MI operation Characteristic phenotype of engrafted ES cells was found in infarcted areas in ES cell transplanted MI rats after 6 week and 32 week follow-ups. With immunofluorescent techniques, these grafted cells were distinct from both normal myocytes and infarcted tissue. The viability of the implanted ES cells was identified by the strongly positive staining to sarcomeric α-actin (FIG. 5D). Positive α-actin identification was not found in the myocardium of sham-operated and cell-free medium injected MI rat hearts.

CONCLUSIONS SUPPORTED BY EMPIRICAL DATA

1. Mammalian embryonic stem cells and their progeny cells can be maintained indefinitely in-vitro as undifferentiated cells; and then prepared at will for implantation purposes using specific medium suitable for subsequent initiation of cell differentiation.
2. The mammalian embryonic stem cells prepared in this manner are suitable for transplantaion purposes in-vivo. These embryonic stem cells can be implanted, survive in-situ, and continue as viable cells in rat infarcted myocardium.

3. The implanted mammalian embryonic stem cells demonstrably improve global cardiac function and contractility of cardiac muscles in-vivo for the living subject after the occurrence of a mycardial infarct in the heart tissues.
4. Rats which underwent myocardial infarction experimentally but received only cell-free culture media subsequently showed much poorer rates of survival after 32 weeks post-infarction in comparison to rats receiving implants of embryonic stem cells.
5. The therapeutic and beneficial results of ES cell implantation in-vivo into the infarcted area of the myocardium—which include a decreased infarcted area and an improved cardiac function as assessed by hemodynamic and echocardiographic measurements—were seen immediately after cell transplantation. The beneficial changes observed 32 weeks after ES cell transplantation were of the same magniutude as those seen at 6 weeks post-implantation.
6. No rejection of ES cells implanted into the infarcted area has been found either at 6 weeks or 32 weeks post-implantation. The methodology thus represents an effective means to repair the damaged myocardium in-situ within a living subject as well as a means for improving ventricular function in post-infarcted hearts.
7. The methodology using ES cells for transplantation thus offers major benefits for long term usage as well as in the short-term. The implanted ES cells demonstrably form stable grafts in-situ and survive as viable cells for an indefiniute period of time within the infarcted area of the myocardium.
8. The implantation of ES cells to an area of myocardial infarction meaningfully provides long-term desirable effects on progressive ventricular remodeling and a substantive improvement of damaged heart function immediatedly after cell transplantation.

The present invention is not to be limited in form nor restricted in scope except by the claims appended hereto.

REFERENCES

1. Eriksson H. Heart failure: a growing public health problem. *J Inter Med* 1995;237:135–141
2. Soonpaa M H, Koh G Y, Klug M G, et al. Formation of nascent intercalated disks between grafted fetal cardiomyocytes and host myocardium. *Science.* 1994;264:98–101.
3. Li R K, Jia Z Q. Weisel R D, et al. Cardiomyocyte transplantation improves heart function. *Ann Thorac Surg.* 1996;62:654–661.
4. Li R K, Mickle D A G, Weisel R D, et al. In vivo survival and function of transplanted rat cardiomyocytes. *Circ Res.* 1996;78:283–288.
5. Li R K, Mickle D A G, Weisel R D, et al. Natural history of fetal rat cardiomyocytes transplanted into adult rat myocardial scar tissue. *Circulation* 1997;96(Suppl II):II179–II187.
6. Bishop S P, Anderson P G, Tucker D C. Morphological development of the rat heart growing in oculo in the absence of hemodynamic work load. *Circ Res* 1990;66:84–102:
7. Hescheler J, Fleishmann B K, Lentini S, et al. Embryonic stem cell: a model to study structural and functional properties in cardiomyocytes. *Cardiovas Res.* 1997;36, 149–162.
8. Kilborn M J, Fedida D. A study of the developmental changes in outward currents of rat ventricular myocytes. *J Physiol Lond.* 1990;430:37–60.
9. Smith A G. Culture and differentiation of embryonic stem cells. *J Tissue Culture Methods.* 1991;13:89–94.
10. Klung M G, Soonpaa M H, Field L J. DNA synthesis and multinucleation in embryonic stem cell-derived cardiomyocytes. *Am J Physiol.* 1995;269:H1913–H1921.
11. Min J Y, Sandmann S, Meissner A, et al. Differential effects of mibefradil, verapamil, and amlodipine on myocardial function and intracellular $Ca^{2-}$ handling in rats with chronic myocardial infarction *J Pharmacol Exp Ther.* 1999;291:1038–1044.
12. Litwin S E, Katz S E, Weinber E O, et al. Serial echocardiographic-Doppler assessment of left ventricular geometry and function in rats with pressure-overload hypertrophy: chronic angiotensin-converting enzyme inhibition attenuates the transition to heart failure. *Circulation* 1995;91:2642–2654.
13. Leenen F H H; Huang B S, Yu H, et al. Brain "Quabain" mediates sympathetic hyperactivity in congestive heart failure. *Circ Res.* 1995;77:993–1000.
14. Litwin S E, Katz S E, Morgan J P, et al. Long-term captopril treatment improves diastolic filling more than systolic performance in arts with large myocardial infarction. *J. Am. Coll. Cardiol.* 1996;28:773–781.
15. Koh G Y, Klung M G, Soonpaa M H, et al. Long-term survival of ATI cardiomyocyte grafts in syngeneic myocardium. *Am J Physiol* 1993;264:H1727–H1733.
16. Chiu R C J, Zibaitis A, Kao R L. Cellular cardiomyoplasty: myocardial regeneration with satellite cell implantation. *Ann Thorac Surg.* 1995,60:12–18
17. Tomita S, Li R K, Weisel R D, et. al. Autologous transplantation of bone marrow cells improves damaged heart function. *Circulation.* 1999;100(Suppl II):II247–1256.
18. Scorsin M, Marotte F Sabri A, et al. Can grafted cardiomyocytes colonize periinfarction myocardial areas? *Circulation* 1996; 94(Suppl II):II337–II340.
19. Midha R, Mackinnon S E, Wade J A; et al. Chronic cyclosporin A therapy in rats. *Microsurgery.* 1992;13:273–276.
20. Robbins J, Doetschman T, Jones W K,et al. Embryonic stem cells as a model for cardiogenesis. *Trends Cardiovasc Med.* 1992;2:44–50.
21. Rathjen P D, Whyatt J L L M, Rathjen B J. Properties and uses of embryonic stem cells: prospects for application to human biology and gene therapy. *Reprod Fertil Dev.* 1998;10:31–47.
22. Pfeffer J M, Pfeffer M A, Branuwald E. Influence of chronic capatopril therapy on the infarcted left ventricle of the rat. *Circ Res.* 1985;57:84–95.
23. Leor J, Patterson M, Quinones M J, et al. Transplantation of fetal myocardial tissue into the infarcted myocardium of rat: a potential method for repair of infarcted myocardium. *Circulation.* 1996;94(Suppl II):II332–II336.
24. Van Meter C H, Claycomb W C, Delcarpio J B, et al. Myoblast transplantation in the porcine model: A potential technique for myocardial repair. *J Thorac Cardioivasc Surg.* 1995;110:1142–1148.
25. Cittadini A, Grossman J D. Napoli R, et al. Growth hormone attenuates early left ventricular remodeling and improves cardiac function in rats with large myocardial infarction *J Am Coll Cardiol.* 1997;29:1109–1116.
26. Leor J, Prentice H, Sartorelli V, et al. Gene transfer and cell transplantation an experimental approach to repair a "broken heart". *Cardiovasc Res* 1997;35:431–441.

What we claim is:

1. A method for improving cardiac function in a mammal after a myocardial infarct, said method comprising the steps of:

maintaining a plurality of undifferentiated mammalian embryonic stem cells in vitro in a culture medium containing at least one selected from the group consisting of leukemia inhibitory factor and fibroblast feeder cells;

subsequently culturing said undifferentiated mammalian embryonic stem cells in vitro in a culture media in the absence of leukemia inhibitory factor and fibroblast feeder cells to yield a cellular inoculum comprising mammalian cells in which differentiation has been initiated;

introducing said cellular inoculum to at least a portion of the previously infarcted area of the heart tissue; and allowing said introduced cellular inoculum to engraft in situ as viable cells situated within the previously infarcted area of the heart tissue, wherein the engraftment results in improved cardiac function in said mammal.

2. A method for improving cardiac function in a mammal after a myocardial infarct, said method comprising the steps of:

obtaining a plurality of undifferentiated mammalian embryonic stem cells;

maintaining said undifferentiated mammalian embryonic stem cells in vitro in a culture medium containing at least one selected from the group consisting of leukemia inhibitory factor and fibroblast feeder cells;

subsequently culturing said undifferentiated mammalian embryonic stem cells for a predetermined time in a culture media in the absence of leukemia inhibitory factor and fibroblast feeder cells to yield a cellular inoculum comprising mammalian cells in which differentiation has been initiated;

introducing said cellular inoculum to at least a portion of the previously infarcted area of the heart tissue; and allowing said introduced cellular inoculum to engraft in situ as viable cells situated within the previously infarcted area of the heart tissue, wherein the engraftment results in improved cardiac function in said mammal.

3. A method for improving cardiac function in a mammal after a myocardial infarct, said method comprising the steps of:

obtaining a plurality of undifferentiated mammalian embryonic stem cells;

maintaining said undifferentiated mammalian embryonic stem cells in vitro in a culture medium containing at least one selected from the group consisting of leukemia inhibitory factor and fibroblast feeder cells;

subsequently culturing said undifferentiated mammalian embryonic stem cells for a predetermined time in a culture media in the absence of leukemia inhibitory factor and fibroblast feeder cells to yield a cellular inoculum comprising mammalian cells in which differentiation has been initiated;

introducing said cellular inoculum to at least a portion of the previously infarcted area of the heart tissue; and allowing said introduced cellular inoculum to engraft in situ as viable cells situated within the previously infarcted area of the heart tissue, wherein the engrafted cells do not cause immunological rejection, and the engraftment results in improved cardiac function in said mammal.

4. The method of claim 1, 2, or 3, wherein said cellular inoculum includes progeny cells of said undifferentiated mammalian embryonic stem cells.

* * * * *